United States Patent [19]

Muhlemann et al.

[11] 4,088,752
[45] May 9, 1978

[54] ORAL COMPOSITION FOR PLAQUE AND CARIES INHIBITION

[75] Inventors: Hans Rudolf Muhlemann, Zurich; Hans Schmid, Muttenz, both of Switzerland

[73] Assignee: Gaba AG, Basel, Switzerland

[21] Appl. No.: 583,125

[22] Filed: Jun. 2, 1975

[30] Foreign Application Priority Data

May 31, 1974 Switzerland ............... 7,516/74

[51] Int. Cl.$^2$ ............... A61K 7/16; A61K 7/18
[52] U.S. Cl. ............... 424/57; 424/52
[58] Field of Search ............... 424/49–58, 424/199; 260/579

[56] References Cited

U.S. PATENT DOCUMENTS

| | | | |
|---|---|---|---|
| 2,069,157 | 1/1937 | Sahyun ............... | 424/57 |
| 2,689,170 | 9/1954 | King ............... | 424/54 |
| 2,757,125 | 7/1956 | Mudrak ............... | 424/54 |
| 2,772,203 | 11/1956 | Salzmann ............... | 424/54 |
| 2,772,204 | 11/1956 | King ............... | 424/54 |
| 2,837,463 | 6/1958 | Fosdick et al. ............... | 424/57 |
| 2,921,886 | 1/1960 | Panepinto ............... | 424/57 |
| 3,029,191 | 4/1962 | King ............... | 424/52 |
| 3,083,143 | 3/1963 | Schmid et al. ............... | 424/52 |
| 3,124,512 | 3/1964 | Schmid et al. ............... | 424/52 |
| 3,277,118 | 10/1966 | Schmid et al. ............... | 424/52 X |
| 3,413,326 | 11/1968 | Schmid et al. ............... | 424/52 X |
| 3,639,571 | 2/1972 | Turesky et al. ............... | 424/54 |
| 3,666,855 | 5/1972 | Muhler ............... | 424/52 |
| 3,699,220 | 10/1972 | Westrate et al. ............... | 424/57 |
| 3,894,147 | 7/1975 | Bahouth ............... | 424/57 |
| 3,959,458 | 5/1976 | Agricola et al. ............... | 424/52 |

OTHER PUBLICATIONS

Goldschmidt Chem. Corp., Dec. 1, 1962, Mfg. Broch., "Tegamine 22 and the Togamine 13 Series," (Phosphoric Acid added for Phosphate Salts also Hydrochloride Citrate Acothic Lactate Salts of Tegamines Dialkylaminoalkyl Fatty Amides–Emulsifiers for Grams) 5 pages.

Scafidi et al., Cosmetics and Perfumery 89:89–91, Apr. 1974, ("Use of Fatty Acid Amido Alkyldimethylamines in Lotions" (with Phosphoric Acid, to Formulate Elegant Creams).

Bass et al., J.Dent. Res. 54(5):972–977, Sep.–Oct. 1975, "Structure Activity Studies on Inhibition of Streptococcus Mutans by Long Chain Aliphatic Diamines".

*Primary Examiner*—Shep K. Rose
*Attorney, Agent, or Firm*—Lowe, King, Price & Markva

[57] ABSTRACT

Oral compositions for plaque and caries inhibition contain a salt of an oxo-acid (formerly called oxy-acid) of phosphorus or a mixed salt of an oxo-acid of phosphorus and hydrofluoric acid with an organic base.

8 Claims, No Drawings

ORAL COMPOSITION FOR PLAQUE AND CARIES INHIBITION

The present invention concerns oral compositions for the care of the mouth and teeth which inhibit the formation of plaque and caries.

It is generally known that oral compositions for the care of the mouth and teeth are intended to contribute through their cleansing action to mouth hygiene and thus to the health of teeth and gums. It has also been shown that it is meaningful to impart oral compositions for the care of the mouth and teeth specific properties over and above this cleansing effect for preventing or combatting pathologic symptoms in the mouth. Such compositions include compositions for preventing caries and paradental diseases as well as, more recently, compositions for inhibiting the formation of bacterially contaminated plaque. The latter is an important causal factor in the mouth illnesses mentioned above. The formulation of such compositions has in fact lead to more or less positive results and to the grant of a series of patents.

In the field of caries-inhibiting oral compositions, the addition of fluorides has proved to be an effective measure. Sodium fluoride, tin fluoride, alkali metal monofluorophosphates and the organic long chain amine hydrofluorides are suitable and mainly used in practice. The latter have proved to be particularly active. The amine hydrofluorides mentioned above, which are described for example in German Pat. No. 1,198,493 and U.S. Pat. No. 3,083,143, are salts of organic bases and hydrofluoric acid. It has now been found that salts of organic bases and oxo-acids (formerly called oxy-acids) of phosphorus also significantly inhibit caries. This finding is surprising for two reasons:

1. Previous and already known investigations with inorganic phosphates, principally sodium phosphate, with and without the addition of fluorides, have shown that these phosphates only make a small contribution to the anti-cariogenic effect.
2. The reduction in the acid solubility of the tooth enamel is an important criterion for caries-reducing action of a substance. This solubility-diminishing effect is in general not ascertainable for the compounds used according to the invention. These compounds nevertheless show a remarkable caries-inhibiting effect.

It has also been found that these amine phosphates inhibit the formation of plaque to a great extent.

The oral compositions of the invention contain salts which are formed by complete or partial neutralization of organic bases with oxo-acids of phosphorus, preferably orthophosphoric, pyrophosphoric and metaphosphoric acids. Of the metaphosphoric acids, the cyclic forms, e.g. trimetaphosphoric acid, have proved to be particularly advantageous.

Owing to the polybasic properties of the phosphoric acids, different degrees of neutralization are possible in the formation of salts. Depending on the chosen stoichiometric ratio between acid and base, acidic, neutral or alkaline salts are obtained. As a rule those phosphates are preferred wherein the pH-value of which is in the acidic to neutral region.

The preparation of the organic salts may be accomplished in simple fashion by the direct action of the free phosphoric acids on the bases. It is advantageous to carry out the reaction in a solvent such as methanol or ethanol and to evaporate the solvent in vacuo. The salts may be obtained as evaporation residues. If the free acids are not available commercially, or are only stable for a short time, they are prepared from their water soluble metal salts by passing the solution through a suitable ion-exchanger. The free acid obtained in disolved form can be reacted with the base immediately after the ion-exchange treatment.

Compounds having the following general formula may be used as the base component:

R — X where R is an alkyl or alkenyl group with 6 – 30 carbon atoms, an alkoxy or alkylol group with 2 – 30 carbon atoms or a substituted or unsubstituted, saturated or unsaturated aralkyl group with an aliphatic chain length of 2 – 30 carbon atoms. Chain lengths of 8 – 20 carbon atoms are preferred.

X can be the following:

(a) $(NH_2)_y$, where $y$ is a integer from 1 to 3;

(b) the grouping

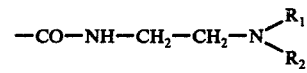

where $R_1$ and $R_2$, which can be the same or different, are hydrogen, acyl, alkyl, alkoxy, alkenyl, alkylol, aralkyl or cycloalkyl groups;

(c) the grouping

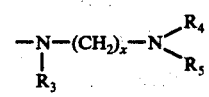

where $R_1$, $R_4$ and $R_5$, which can be the same or different, are hydrogen, acyl, alkyl, alkoxy, alkenyl, alkylol, aralkyl or cycloalkyl groups and $x$ is an integer from 1 to 3;

(d) the grouping

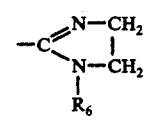

where $R_6$ is hydrogen, an acyl, alkyl, alkoxy, alkenyl, alkylol, aralkyl or a cycloalkyl group;

(e) the grouping

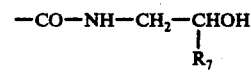

where $R_7$ is hydrogen or a lower alkyl group; or (f) the grouping

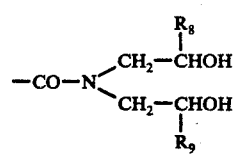

where $R_8$ and $R_9$, which can be the same or different, are hydrogen or lower alkyl groups.

If polyvalent bases, i.e. bases with at least 2 nitrogen atoms and sufficiently high basicity, are used, it is possible to obtain mixed salts. For the purpose of this invention it is advantageous to neutralize one of the basic groups with hydrogen fluoride and the remaining one with one of the phosphoric acids. Such organic hydrofluoride phosphates can be prepared with compounds of the types (c) and (d) for instance.

The following examples illustrate methods of preparing some organic phosphates and hydrofluoride phosphates.

EXAMPLE 1

Preparation of
N,N,N'-tris-(2-hydroxyethyl)-N'-octadecyl-1,3-diaminopropane trimethaphosphate Addition ratio of amine:acid = 1.5:1

To prepare a solution of trimetaphosphoric acid, 0.05 mole (15.3g) of sodium trimetaphosphate dissolved in 15 ml of water is introduced onto a column packed with an ion-exchange resin [Amberlite IR-120, strongly acidic ion-exchanger of Fluka (Switzerland), 500 g] and the column washed neutral with water. The volume of the collected acid is made up to 500 ml.

0.075 mole (34.35g) of the ethoxylated diamine is dissolved in 200 ml of ethanol and the previously prepared trimetaphosphoric acid solution (500 ml) is added to it while stirring. When all the trimetaphosphoric acid solution has been added, the solvent is evaporated and the product is obtained as a tough, amorphous mass which cannot be recrystallized from any solvent.

EXAMPLE 2

Preparation of
tris-[N,N,N'-tris-(2-hydroxythyl)-N'-octadecyl-1,3-diaminopropane monohydrofluoride]-trimetaphosphate Addition ratio of amine monohydrofluoride:acid = 3:1

To prepare a solution of trimetaphosphoric acid, 0.05 mole (15.3g) of sodium trimetaphosphate dissolved in 15 ml of water are introduced onto a column packed with an ion-exchange resin (Amberlite IR-120, strongly acidic ion-exchanger of Fluka) and the column washed neutral with water. The volume of the collected acid is made up to 500 ml. The yield is practically quantitative.

0.15 mole (68.7g) of the ethoxylated diamine is dissolved in 200 ml of methanol and 0.15 mole of hydrofluoric acid (7.5g of 40% aqueous acid) added. The resulting solution is stirred for some time and the previously prepared trimetaphosphoric acid solution is then added. When all the trimetaphosphoric acid has been added the solvent is evaporated in vacuo and the product is obtained as a tough, amorphous mass which cannot be crystallised.

EXAMPLE 3

Preparation of
N,N,N'-tris-(2-hydroxyethyl)-N'-octadecyl-1,3-diaminopropane diorthophosphate Addition ratio of amine:acid = 1:2

0.1 mole (45.8g) of the ethoxylated diamine is dissolved in 200 ml of methanol. 0.2 mole of phosphoric acid (23.05 g of 85% acid) is added dropwise while stirring. When all the phosphoric acid has been added the resulting solution is stirred for some time and the reaction mixture evaporated in vacuo. The product is left as a tough, amorphous mass which cannot be crystallised. The yield is practically quantitative.

EXAMPLE 4

Preparation of
N,N,N'-tris-(2-hydroxyethyl)-N'-octadecyl-1,3-diaminopropane monohydrofluoride monoorthophosphate Addition ratio of amine monohydrofluoride:phosphoric acid = 1:1.

0.1 mole (45.8g) of the ethoxylated diamine is dissolved in 200 ml of methanol in a plastic vessel (e.g. a polythene vessel). The monohydrofluoride is first prepared by adding 0.1 mole of hydrofluoric acid (5g of 40% aqueous acid) while stirring. The use of glass equipment must be avoided. The resulting solution is stirred for some time and 0.1 mole of phosphoric acid (11.52 g of 85% aqueous acid) is then added. When all the phosphoric acid has been added the solution is again stirred for some time and the reaction mixture is then evaporated in vacuo. The product is left as a tough, amorphous mass which cannot be crystallised from any solvent. The yield of raw product is practically quantitative.

EXAMPLE 5

Preparation of octadecen-9-ylamine orthophosphate

Addition ratio of amine:acid = 1:1

0.1 mole (26.8g) of octadecen-9-ylamine (oleylamine) is dissolved in 100 ml of ethanol and 0.1 mole of phosphoric acid (11.52g of 85% aqueous acid) is added dropwise while stirring. After all the phosphoric acid has been added the resulting solution is stirred for some time. 50 ml of acetone is then added and the resulting product filtered off with a suction filter, washed with a little petroleum ether and reprecipitated once from ethanol. The product sinters at 110° C.

EXAMPLE 6

Preparation of
N-(2-hydroxyethyl)-2-heptadecen-9-yl-imidazoline orthophosphate

Addition ratio of amine:acid = 1:1

0.1 mole (34.8g) of N-(2-hydroxyethyl)-2-heptadecen-9-yl-imidazoline is dissolved in 200 ml of methanol and 0.1 of mole phosphoric acid (11.52g of 85% aqueous acid) is added dropwise while stirring. When all the phosphoric acid has been added the resulting solution is stirred for some time and the solvent evaporated in vacuo. The product is left as a honey-like mass. The yield is practically quantitative.

EXAMPLE 7

Preparation of
N,N,N'-tris-(7-hydroxyethyl)-N'-octadecyl-1,3-diaminopropane pyrophosphate Addition ratio amine:acid = 1:1

0.1 mole of the ethoxylated diamine is dissolved in 200 ml of methanol. A solution of 0.1 mole (18g) of pyrophosphoric acid in 20 ml of water is added dropwise while stirring. When all the pyrophosphoric acid has been added the resulting solution is stirred for some time and the reacation mixture is then evaporated. The product is left as a tough, amorphous, uncrystallisable mass. The yield of raw product is practically quantitative.

To examine the effect of the compounds used according to the present invention, a series of animal experiments were carried out. In these tests an aqueous solution of the test compounds was applied locally to determine its action in inhibiting plaque and caries. As well as control experiments with the pure solvent (water), comparisons where also carried out with sodium fluoride as well as with NaF+monosodium orthophosphate ($NaH_2PO_4$).

Groups of 10 Osbourne-Mendel rats, which are particularly suitable for caries-inhibition studies, were subjected to the following treatments:

1. Control, $H_2O$
2. Control, $H_2O$
3. NaF solution, 250 ppm F
4. Sodium trimetaphosphate (TMP) 3%
5. NaF, 250 ppm F + TMP 3%
6. Compound from Example 1, same P-concentration as in 4
7. Compound from Example 2, 250 ppm F
8. Compound from Example 3, same P-concentration as in 4
9. Compound from Example 4, 250 ppm F
10. NaF, 250 ppm F + $NaH_2PO_4.2H_2O$, same P-concentration as in 4.

On day 13 the animals with their dams were transferred to stainless-steel cages and fed powdered Nafag diet. The animals were weaned when 22 days old and distributed at random among the treatments.

0.1 ml of the test solutions were applied once daily during the whole 20-day experimental period in which diet 2000a and tap water were available ad libitum. On day 22 the animals were superinfected twice with Streptococcus mutans OMZ 176. Caries, molar surface dissolution rate and fluoride content were assessed acccording to routine procedures.

RESULTS

1. Growth:

The treatments had no significant effects on the weight gains during the 20-day experimental period.

2. Smooth surface plaque:

The average extent was significantly lower ($P_F<0.001$) in the animals of treatments 6 and 8.

3. Smooth surface caries:

All compounds significantly inhibited smooth surface caries. Both sodium fluoride and sodium trimetaphosphate were effective and their cariostatic effects were additive.

4. Fissure caries:

The average fissure caries incidence was significantly ($P_F<0.05$) lower in the animals of treatments 4 to 6 and 8 to 10 than in the animals of the control groups.

5. Molar surface dissolution rate:

While sodium fluoride significantly ($P_F<0.05$) decreased the molar surface dissolution rate, all other compounds had no significant effects on the dissolution rate.

6. Molar surface fluoride content

The average fluoride content of the molar surfaces of the animals treated with fluoride containing compounds was significantly higher than that of the molar surfaces of the animals treated with fluoride free compounds.

Table I

Average number per rat of smooth surface plaque extent (PU), advanced dentinal fissure lesions (B), smooth surface carious units (E) and weight gains (g) during the 20-day experimental period

| Treatments | PU | B | E | g |
|---|---|---|---|---|
| 1 | 2.4 | 10.2 | 17.2 | 62 |
| 2 | 3.1 | 10.8 | 17.0 | 65 |
| 3 | 2.5 | 9.8 | 9.0 | 65 |
| 4 | 2.7 | 6.1 | 10.1 | 60 |
| 5 | 3.2 | 6.2 | 4.6 | 55 |
| 6 | 1.5 | 5.3 | 4.0 | 65 |
| 7 | 2.1 | 8.2 | 11.1 | 64 |
| 8 | 0.8 | 4.9 | 3.0 | 52 |
| 9 | 2.1 | 5.4 | 4.7 | 61 |
| 10 | 2.6 | 7.8 | 8.5 | 67 |
| Means of 10 animals with a standartd error $s_{\bar{x}}$ of: | | | | |
| | 0.29 | 0.94 | 1.81 | 3.4 |

Table II

Postmortal rat molar solubility ($\mu gP$ per mand: $m_1 + m_2$ in 10 ml 0.025 M acetate buffer pH 4, 60 min., 37° C). Fluoride concentrations in the first, the second and the first and second cumulated layers (ppm F) in the maxillary molars ($m_1 + m_2$, 15 sec. in 2N hydrochloric acid under agitation)

| Treatments | $\mu gP$ | First layer ppm F | Second layer ppm F | Cumulated layers ppm F |
|---|---|---|---|---|
| 1 | 134 | 96 | 43 | 72 |
| 2 | 130 | 98 | 59 | 80 |
| 3 | 121 | 242 | 94 | 170 |
| 4 | 130 | 92 | 53 | 74 |
| 5 | 113 | 221 | 95 | 161 |
| 6 | 134 | 83 | 39 | 61 |
| 7 | 137 | 187 | 94 | 143 |
| 8 | 152 | 107 | 49 | 79 |
| 9 | 123 | 199 | 77 | 142 |
| 10 | 133 | 165 | 80 | 123 |
| Means of 1Q determinations with a standard error $s_{\bar{x}}$ of: | | | | |
| | 5.7 | 16.6 | 10.4 | 12.4 |

The compounds using according to the invention can be incorporated into oral compositions for the care of the mouth and teeth such as toothpastes, transparent pastes, gels, mouth rinses, sprays and chewing gum. In the case of liquid or paste compositions the fact must be taken into account that the present compounds show more or less cationic properties and particularly the long-chain compounds tend to display incompatibilities with anionic agents. This particularly applies to the addition of foamers and hydrocollodial binders. Thus non-ionic or cationic compounds are preferably used with these excipients.

Toothpastes are basically made up according to the system: abrasives/binders/softeners and humectants/detergents/flavouring and aroma agents.

The following are preferred for use as abrasives: Alkaline earth phosphates, e.g. dicalcium phosphate dihydrate, anhydrous dicalcium phosphate, insoluble alkali metal metaphosphates, finely ground silicon dioxides, hydrated aluminum oxides and aluminium silicates. These abrasives are usually added in the proportion 25 - 60%, preferably 30 - 45%, based on the complete paste composition.

The binders are gelling agents. Suitable binders are non-ionic cellulose ethers such as methyl cellulose, hydroxyalkylcellulose (e.g. methyl, ethyl, propyl cellulose), guar gum, highly collodial silicic acid (aerosils) and bentonites.

Polyhydric alcohols such as glycerol, sorbitol, mannitol, glucose syrup and propylene glycol are suitable as softeners and humectants.

The addition of detergents is advisable in those cases in which a strongly foaming tooth-care composition is required. The long-chain members of the compounds used according to the invention already have in themselves detergent character. They thus allow the manufacture of tooth-care compositions without using additional, foam-producing detergents. If such an addition is required for particular reasons however, the question of the use of an anionic, non-ionic or cationic foamer must first be cleared up by an compatibility test. Non-ionic compounds are preferred such as imidazoline derivatives, polyoxy-ethylene esters, fatty amines having the betaine structure [e.g. Tego-Betaines from Goldschmidt, (Germany)], sucrose esters, amine oxides, ethers of polyethylene glycols and straight-chain alcohols.

As flavouring agents, saccharin, quaternary ammonium saccharinates, coumarin and vanillin are suitable, and as aroma agents mixtures of the essential oils usually employed. Peppermint oil, spearmint oil, aniseed oil, menthol and anethol generally are the main flavouring components, and cinnamon oil and methyl salicylate etc. may be added.

The liquid compositions consist of an aqueous or preferably an aqueous-alcoholic solution of the compounds used according to the invention, together with the usual additives such as flavouring and aroma agents, emulsifiers and wetting agents of a compatible nature, glycerol, sorbitol, and plant extracts.

Some illustrative examples of oral compositions for the care of the mouth and teeth according to the present invention are given below:

EXAMPLE 8, TOOTHPASTE

| | |
|---|---|
| N,N,N'-tris-(2-hydroxyethyl)-N'-octadecyl-1,3-diaminopropane diorthophosphate | 1.500 % |
| hydroxyethyl cellulose | 2.100 % |
| sorbitol syrup, 70 % | 12.000 % |
| Aroma agents | 1.500 % |
| titanium dioxide | 1.000 % |
| dicalcium phosphate dihydrate | 35.000 % |
| water | 46.900 % |

The pH-value of this paste is 5.1

EXAMPLE 9, TOOTHPASTE

| | |
|---|---|
| N,N,N'-tris-(2-hydroxyethyl)-N'-octadecyl-1,3-diaminopropane monohydrofluoride monoorthophosphate | 1.500 % |
| guar gum | 1.800 % |
| sorbitol syrup, 70 % | 12.000 % |
| aroma agents | 1.500 % |
| titanium dioxide | 1.000 % |
| sodium methaphosphate, insoluble | 30.000 % |
| water | 52.200 % |

The pH-value of this paste is 3.9.

EXAMPLE 10, TOOTHPASTE

| | |
|---|---|
| Octadecen-9-ylamine orthophosphate | 1.500 % |
| hydroxyethyl cellulose | 1.650 % |
| glycerol | 50.000 % |
| aroma agents | 1.500 % |
| silicic acid | 16.000 % |
| water | 29.350 % |

The pH-value of this paste is 4.8.

These toothpastes may be prepared as follows:

The cellulose ether or the guar gum is dissolved in a slime in part of the water. The active substance, dissolved in the remaining water, is then added. The glycerol, the abrasive and if necessary the wetting or foaming agent are then incorporated. The resulting mass is thoroughly mixed in a suitable mixer and if necessary homogenised in a roller mill or a colloid mill.

EXAMPLE 11, MOUTH RINSE

| | |
|---|---|
| N-(2-hydroxyethyl)-2-heptadecen-9-yl-imidazoline orthophosphate | 0.250 % |
| aroma agents | 0.070 % |
| polyoxyethylenesorbitan monooleate | 1.000 % |
| ethanol | 20.000 % |
| water | 78.680 % |

This mouth rinse can be prepared as follows:

The active substance is dissolved with gentle warming in about ¾ of the water. The aroma agents are emulsified in the polyoxoyethylenesorbitan monooleate and this emulsion dissolved in the alcohol-water mixture (all the alcohol and the remaining water). Both solutions are then mixed well together.

We claim:

1. An oral fluoride-free dentifrice composition selected from the group consisting of toothpastes, transparent toothpastes, gels, mouth rinses, sprays, and chewing gum, for plaque and caries inhibition, said composition containing a salt formed by reaction of an oxo-acid of phosphorus with an organic amine base, said organic amine base being of the formula R-X, where R is selected from the group consisting of an alkyl group having 6 to 30 carbon atoms, an alkenyl group having 6 to 30 carbon atoms, an alkoxy group having 2 to 30 carbon atoms, an alkylol group having 2 to 30 carbon atoms, a substituted or unsubstituted, saturated or unsaturated aralkyl group substituted with an alkyl group having a chain length of 2 to 30 carbon atoms, and X is selected from the group consisting of:

(a) $(NH_2)_y$, where y is an integer from 1 to 3, (b) the grouping

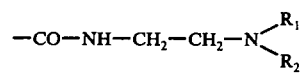

where $R_1$ and $R_2$, which can be the same or different, are selected from the group consisting of hydrogen, acyl, alkyl, alkoxy, alkenyl, alkylol, aralkyl and cycloalkyl groups, (c) the grouping

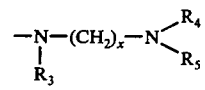

where $R_3$, $R_4$ and $R_5$, which can be the same or different, are selected from the group consisting of hydrogen, acyl, alkyl, alkoxy, alkenyl, alkylol, aralkyl and cycloalkyl groups, and x is an integer from 1 to 3, (d) the grouping

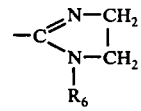

where $R_6$ is selected from the group consisting of hydrogen, acyl, alkyl, alkoxy, alkenyl, alkylol, aralkyl and cycloalkyl groups, (e) the grouping

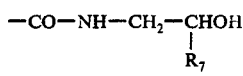

where $R_7$ is selected from the group consisting of hydrogen and lower alkyl groups, and (f) the grouping

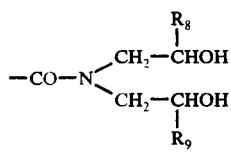

where $R_8$ and $R_9$, which can be the same or different, are selected from the group consisting of hydrogen and lower alkyl groups.

2. A composition according to claim 1 wherein the oral composition is a toothpaste.

3. A composition according to claim 1 wherein the oral composition is a mouth rinse.

4. A composition according to claim 1 wherein the oxo-acid of phosphorus is selected from the group consisting of orthophosphoric acids, pyrophosphoric acids and metaphosphoric acids.

5. A composition according to claim 1 wherein $x$ has the formula:

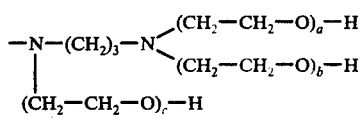

where $a$, $b$ and $c$ are the same or different numbers with a mean value such that the sum $a + b + c = 3$ to 36.

6. A composition according to claim 1 wherein R is selected from the group consisting of alkyl groups of 14 to 18 carbon atoms and mixtures of alkyl groups having 14 to 18 carbon atoms.

7. A composition according to claim 4 wherein the oxo-acid of phosphorus is a cyclic metaphosphoric acid.

8. A composition according to claim 6 wherein R is a tallow-alkyl group.

* * * * *